United States Patent
Bollenbeck et al.

(10) Patent No.: US 11,982,727 B2
(45) Date of Patent: May 14, 2024

(54) PILOT TONE SIGNAL GENERATOR, MAGNETIC RESONANCE TOMOGRAPH, METHOD FOR TRANSMISSION OF A SYNCHRONIZATION SIGNAL AND COMPUTER PROGRAM PRODUCT

(71) Applicant: Siemens Healthineers AG, Forchheim (DE)

(72) Inventors: Jan Bollenbeck, Eggolsheim (DE); Peter Speier, Erlangen (DE); Mario Bacher, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 0 days.

(21) Appl. No.: 17/897,893

(22) Filed: Aug. 29, 2022

(65) Prior Publication Data
US 2023/0082926 A1   Mar. 16, 2023

(30) Foreign Application Priority Data
Sep. 10, 2021   (EP) .................................. 21195956.4

(51) Int. Cl.
| G01R 33/565 | (2006.01) |
| A61B 5/055 | (2006.01) |
| G01R 33/36 | (2006.01) |
| G01R 33/567 | (2006.01) |

(52) U.S. Cl.
CPC ........ *G01R 33/56509* (2013.01); *A61B 5/055* (2013.01); *G01R 33/3692* (2013.01); *G01R 33/5673* (2013.01); *G01R 33/3621* (2013.01)

(58) Field of Classification Search
CPC .......... G01R 33/56509; G01R 33/3692; G01R 33/5673; G01R 33/362; G01R 33/3642; A61B 5/055; A61B 5/1126; A61B 5/7214
See application file for complete search history.

(56) References Cited

U.S. PATENT DOCUMENTS

| 4,740,750 A | * | 4/1988 | Machida ............ G01R 33/3621 324/309 |
| 10,222,443 B2 | | 3/2019 | Bollenbeck et al. |
| 10,393,845 B2 | | 8/2019 | Schröter et al. |
| 2016/0245888 A1 | | 8/2016 | Bollenbeck |

(Continued)

FOREIGN PATENT DOCUMENTS

| EP | 3742184 A1 | 11/2020 |
| WO | 2004089211 A2 | 10/2004 |

OTHER PUBLICATIONS

Wikipedia "Inverse-square Law" Retrieved Aug. 1, 2022. pp. 1-8. https://en.wikipedia.org/wiki/Inverse-square_law.

(Continued)

*Primary Examiner* — Rishi R Patel
(74) *Attorney, Agent, or Firm* — Lempia Summerfield Katz LLC

(57) ABSTRACT

A pilot tone signal generator, a magnetic resonance tomograph, a method for transmission of a synchronization signal, and a computer program product are disclosed. The pilot tone signal generator includes a receive unit for receipt of a synchronization signal of a system control unit of a magnetic resonance tomograph. The synchronization signal may include a clock signal, and the pilot tone signal generator is configured to emit a pilot tone signal as a function of the synchronization signal.

15 Claims, 6 Drawing Sheets

(56) References Cited

U.S. PATENT DOCUMENTS

| | | |
|---|---|---|
| 2017/0160367 A1 | 6/2017 | Schröter |
| 2017/0176552 A1 | 6/2017 | Reykowski |
| 2020/0396112 A1* | 12/2020 | Biber ..................... A61B 5/055 |
| 2022/0206098 A1 | 6/2022 | Leussler et al. |
| 2022/0413073 A1* | 12/2022 | Bollenbeck .......... G01R 33/482 |

OTHER PUBLICATIONS

Wikipedia "Photodiode" Retrieved Aug. 1, 2022. pp. 1-10. https://en.wikipedia.org/wiki/Photodiode.

* cited by examiner

PILOT TONE SIGNAL GENERATOR, MAGNETIC RESONANCE TOMOGRAPH, METHOD FOR TRANSMISSION OF A SYNCHRONIZATION SIGNAL AND COMPUTER PROGRAM PRODUCT

The present patent document claims the benefit of European Patent Application No. 21195956.4, filed Sep. 10, 2021, which is hereby incorporated by reference in its entirety.

TECHNICAL FIELD

The disclosure relates to a pilot tone signal generator, a magnetic resonance tomograph, a method for transmission of a synchronization signal, and a computer program product.

BACKGROUND

Magnetic resonance tomographs (MRT) are imaging apparatuses, which for imaging of an examination object, (e.g., a human or an animal patient), align nuclear spins of the examination object with a strong external magnetic field ($B_0$ field) and excite them by a magnetic alternating field ($B_1$ field) for precession about this alignment. The precession or return of the nuclear spins from this excited state into a state with lower energy in its turn creates as a response a magnetic resonance signal in the form of a magnetic alternating field, which may be received via the receive coils. To receive this magnetic resonance signal local receive coils, known as local coils, may be used, which are arranged directly on the examination object to achieve an enhanced signal-to-noise ratio (SNR).

With the aid of magnetic gradient fields, a spatial encoding is applied to the signals, which subsequently makes possible an assignment of the received magnetic resonance signal to a volume element. The received magnetic resonance signal may then be reconstructed in order to create one or more magnetic resonance images.

U.S. Pat. No. 10,222,443 B2 discloses a method that makes it possible to trigger timed execution sequences during a magnetic resonance examination in response to physiological movements, such as breathing and/or heartbeat. This enables movement artifacts to be avoided (prospective movement correction) and/or to be rectified in the course of digital post processing (retrospective movement correction). It is proposed that a weak, sufficiently constant radio-frequency (RF) pilot tone signal, in particular constant in respect of amplitude and/or frequency, be emitted during the magnetic resonance examination in such a way that the tone may be received via one or more receive coils, without disturbing the receipt of the magnetic resonance signal. The detection of patient movements occurs via the evaluation of the temporal course of amplitude and/or phase of the received pilot tone signal. A pilot tone signal generator for emitting a pilot tone signal is described, for example, in U.S. Pat. No. 10,393,845 B2.

SUMMARY AND DESCRIPTION

The object of the present disclosure may be seen as providing a pilot tone signal generator, which makes possible an enhanced movement correction. In particular, it is desirable to make a more exact evaluation of the pilot tone signal possible.

The scope of the present disclosure is defined solely by the appended claims and is not affected to any degree by the statements within this summary. The present embodiments may obviate one or more of the drawbacks or limitations in the related art.

Accordingly, a pilot tone signal generator is proposed, wherein the pilot tone signal generator includes a receive unit for receipt of a synchronization signal of a system control unit of a magnetic resonance tomograph. In this case, the synchronization signal includes a clock signal, and the pilot tone signal generator is embodied to emit a pilot tone signal as a function of the synchronization signal.

The pilot tone signal generator may be configured to emit the pilot tone signal into an examination object as an electromagnetic radio-frequency signal. A pilot tone signal receiver, (e.g., a local coil and/or a body coil permanently installed in the magnetic resonance tomograph), may be configured to receive the pilot tone signal and to transmit information about a physiological process in the examination object and/or a movement of the examination object to an evaluation unit for evaluation.

The pilot tone signal generator may be part of a local coil, in particular may be integrated and/or built into a local coil. Advantageously, this enables the pilot tone signal generator to be positioned especially close to the examination object, so that advantageously a pilot tone signal received again after the emission by the pilot tone signal generator, for example, by receive antennas of the local coil, has an especially high SNR.

The generated pilot tone signal may have a first frequency band, wherein the pilot tone signal receiver, in particular the pilot tone signal receiver, is embodied to accept a receive frequency band that includes the first frequency band. The magnetic resonance tomograph may include a radio-frequency unit, which is embodied to output a radio-frequency pulse with a second frequency band, wherein a magnetic resonance signal of the radio-frequency pulse is acquired with the pilot tone signal receiver, wherein the magnetic resonance signal has a third frequency band, which lies at least outside the first frequency band. Advantageously the first frequency band does not collide with the actual measurement signal, the magnetic resonance signal, which lies in the third frequency band.

The clock signal may be a clock signal, (e.g., a reference clock signal), of the magnetic resonance tomograph. The clock signal may be configured to transmit a reference clock of the magnetic resonance tomograph. Advantageously, the pilot signal is linked phase-synchronously to the reference clock of the magnetic resonance tomograph. Advantageously this enables fluctuation in an uncontrolled manner of the absolute phase of the pilot signal in relation to the reference clock of the magnetic resonance tomograph to be avoided. The absolute phase may thus be evaluated. Any restriction of the phase evaluation to the relative phases between receive channels may be overcome by this. Instead, phase information of a receive channel or of a combination of channels, which serves as a reference, may be evaluated. Further SNR losses in the pilot tone phase may be avoided by differentiation of a plurality of measurement signals.

Depending on detection of the pilot signal phase fluctuations translate during lowpass filtering into amplitude fluctuations. A synchronization by the synchronization signal enables phase fluctuations to be reduced, so that the received amplitude of the pilot signal also becomes more stable.

One form of embodiment of the pilot tone signal generator makes provision for the synchronization signal to be an optical data signal, wherein the receive unit includes a first sensor for receiving the optical data signal from the environment of the pilot tone signal generator and is embodied to create an electrical sensor signal from the optical data signal.

The optical data signal may not only be a signal in a wavelength visible to the human eye of 380 nm to 750 nm, but also in adjacent wavelength ranges such as ultraviolet between 150 nm and 380 nm or near infrared between 750 nm and 2000 nm. In particular, the optical data signal has a wavelength of between 780 nm and 1000 nm. In particular, the energy of the light quantas is greater than 0.8 eV.

The environment in this case is seen as the free space surrounding the pilot tone signal generator, in particular in a position in accordance with the application, for example, in a patient tunnel. In particular, it is not understood as any connection such as an optical waveguide routed between pilot tone signal generator and magnetic resonance tomograph.

The first sensor may convert the optical data signal into an electrical signal, which is further used in the pilot tone signal generator to create a pilot tone signal. The optical data signal may transmit information from the magnetic resonance tomograph to the pilot tone signal generator. The sensor may have a photodiode, a phototransistor, or another electronic element as a detector element or be a combination of electronic components, for example, with an amplifier, which converts an optical signal into an electrical signal or sensor signal.

In an advantageous way, the wireless pilot tone signal generator allows a transmission via the optical sensor of information for control of the pilot tone signal generator without disturbing the magnetic resonance receipt or without cables disrupting the operation of the magnetic resonance tomograph.

A further form of embodiment of the pilot tone signal generator makes provision for the receive unit to include a second sensor adjacent to the first sensor, wherein the first sensor is designed to create a first output signal from the optical data signal and the second sensor is designed to create a second output signal from the same optical data signal, wherein the first output signal has an inverse amplitude to the second output signal, wherein the pilot tone signal generator has an inverter, which inverts the output signal of the first sensor, and a summation element, which is designed to add the inverted output signal of the first sensor and the output signal of the second sensor to the sensor signal.

In particular, a spacing between the first sensor and the second sensor may be seen as adjacent in this case, in which the electrical and/or magnetic fields created by the magnetic resonance tomograph have the same strength, so that disruptions caused by these fields in the first and the second sensor are identical. The spacing may be less than 2 mm, 5 mm, 1 cm, or 5 cm. The sensors may be arranged or aligned so that an optical signal source in an environment of the pilot tone signal generator has a similar effect in a detector element of the first sensor and the second sensor, in particular, as regards the strength or the amount obtained, for example, create an approximately equal number of electron-hole pairs in the two sensors.

The first sensor may be configured to create a first output signal from the optical data signal and the second sensor is designed to create a second output signal from the same optical data signal. The first output signal may have an inverted amplitude to the second output signal, in other words the amount is the same, but the leading sign is different. In this case, the output signal is considered with regard to or relative to an idle level or offset that the first sensor and the second sensor creates for example without the effect of an optical signal, or as an alternating current component of a signal created by the sensor with frequency components greater than 1 Hz, 100 Hz, 1 kHz, 100 kHz, or 1 MHz. Opposing leading signs may be achieved by a photodiode in the first sensor being connected to the positive supply voltage and via a resistor to the negative supply voltage, while a photodiode in the second sensor is connected to the negative supply voltage and is connected via a resistor to the positive supply voltage. The output signal with different leading signs is then present in each case at the connection points of the photodiodes with the resistors.

The pilot tone signal generator may include an inverter, which inverts the output signal of the first sensor, and a summation element, which is configured to add the inverted output signal of the first sensor and the output signal of the second sensor to a sensor signal. An inversion of the signal may be achieved by an emitter circuit with a transistor.

In an advantageous way, output signals created by optical signals by the inverse leading sign and the subsequent inverting with the same leading sign are added and, in this way, amplified, while electrically and/or magnetically induced disruptions caused by the simple inverting may be rectified during the summation, so that the interference component in the sensor signal is significantly reduced.

The synchronization signal, in particular the clock signal, may have an amplitude modulation, wherein the pilot tone signal generator is embodied to demodulate the optical data signal.

The pilot tone signal generator may include a filter, which is configured to select a carrier signal frequency or a first modulation frequency of the sensor signal. In other words, the filter has a local or additionally, in some examples, a global minimum of an insertion loss for a predetermined carrier signal frequency. The filter may attenuate a sensor signal with a frequency at a distance of an octave or at a frequency the same as half of or double the carrier signal frequency in relation to attenuation at the modulation frequency by more than 24 dB, 30 dB, or 36 dB. The filter may be a bandpass filter, or a lowpass filter, depending on frequency spectrum of the modulation of the optical signal.

A further embodiment of the pilot tone signal generator makes provision for the pilot tone signal generator to include an, in particular narrowband, Phase-Locked Loop circuit (PLL circuit) for synchronization of the pilot tone signal, wherein a signal derived from the sensor signal serves as reference signal for the Phase-Locked Loop circuit.

A further form of embodiment of the pilot tone signal generator makes provision for the pilot tone signal generator to have a filter that is designed to select a modulation frequency of the sensor signal, wherein the, in particular narrowband, PLL circuit is configured to stabilize an oscillator as a function of the modulation frequency, and, e.g., of the modulation phase.

For example, the narrowband PLL circuit is configured to stabilize an oscillator, (e.g., a quartz oscillator and/or a voltage-controlled oscillator (VCO)), as a function of the carrier signal frequency. The quartz oscillator may be a voltage-controlled crystal oscillator (VCXO). With voltage-controlled oscillators, an oscillator frequency may advantageously be changed by applying an electrical voltage. A narrowband PLL circuit here is in particular a PLL circuit, which locks at a frequency deviation from the oscillator's own frequency of less than 100 ppm, 10 ppm, or 1 ppm.

Advantageously, a narrowband PLL circuit is fault tolerant and may provide a precise clock signal even with brief outliers of the sensor signal.

A further form of embodiment of the pilot tone signal generator makes provision for the pilot tone signal generator to include a filter that is designed to select an odd-number harmonic of an output signal of the PLL circuit. If, for example, the output signal of the PLL circuit has a frequency of 12.5 MHz, then the selected harmonic may in particular be a fifth harmonic, which has a frequency of 62.5 MHz (equal to 5 times 12.5 MHz).

The oscillator, (e.g., the VCXO), has a rectangular waveform characteristic. The signal spectrum thus contains primarily harmonics of odd-number order. Thus, such oscillators are especially well suited for selecting an odd-number harmonic. Via a bandpass filter, for example, an odd-number harmonic (such as the fifth harmonic), may be selected herefrom and supplied to a transmit antenna, (e.g., a small conductor loop), of the pilot tone signal generator for emission. The magnetic alternating field created in this way may couple into the receive antennas, (e.g., receive antennas arranged in local coils), of the magnetic resonance tomograph.

In one embodiment of the pilot tone signal generator, the pilot tone signal generator has an amplitude demodulator with a compensation circuit. The compensation circuit is configured to compensate for a low-frequency signal component of the sensor signal compared to a modulation frequency of the modulation signal. A spectral component of the signal demodulated by the amplitude demodulator may be seen as a low-frequency component, the frequency of which is less than 10%, 1%, or a permille of the modulation frequency. In other words, the frequency of which is less than 10%, 1%, or a permille of the useful signal to be transmitted, e.g., of the synchronization signal, in particular, of the clock signal and/or control signal. In particular, components may be seen as low-frequency, which are caused by movements of the pilot tone signal generator (for example, through movements of a local coil, in which the pilot tone signal generator is arranged) during use or through external light sources and are in the range below 200 Hz, 120 Hz, or 60 Hz.

Changes in intensity through movement or shading may be slow signal changes, which, as a result of this frequency difference, may advantageously be separated by a compensation circuit from a clock frequency or a data signal and/or suppressed.

In one embodiment of the pilot tone signal generator, the compensation circuit includes a comparator with a reference voltage input, which via a lowpass is in a first signaling connection to the sensor signal. In particular, the compensation circuit has a differential amplifier connected as a comparator to a reference voltage input, which is connected via an attenuation element, e.g., in the form of a resistive voltage divider in a series circuit with a lowpass, in a first signal connection to the sensor signal. In this case, a circuit that compares two input signals and for a slight difference between the input signals already provides a comparison result in the form of a turned-on output voltage may be seen as a comparator. The comparator in this regard corresponds to a differential amplifier with a high gain. It is conceivable in this case for the reference voltage input not to be inverting, and for the sensor signal or a signal proportional thereto to be present at the inverting input of the differential amplifier.

In this way, only the low-frequency components in the sensor signal are applied as the comparator reference signal to the non-inverting input of the differential amplifier via the lowpass. Hereby, the comparator reference signal in an advantageous way follows slow changes, as arise from movement or shading. An upstream voltage divider may reduce the voltage of the lowpass-filtered reference signal, so that this lies without control signal transmission below the sensor voltage and the comparator output signal reacts exclusively to the portion in the sensor signal brought about by the swiftly changing modulation signal.

In one embodiment of the pilot tone signal generator, the first signal connection has a track-and-hold element, which is actuated as a function of a differential voltage between sensor signal and reference voltage. For example, an electronic switch may be arranged between a source of the sensor signals and the lowpass.

In an advantageous way, the switch then disconnects the sensor signal path to the lowpass when a sensor signal voltage is below the reference voltage because of the rapid modulation, whereby the reference voltage is kept constant until such time as the sensor signal voltage again exceeds the reference voltage because of the modulation content.

In one embodiment of the pilot tone signal generator, the synchronization signal includes a control signal, wherein the pilot tone signal generator includes a control component configured to control, with the aid of the control signal, an amplitude and/or phase of the pilot tone signal. Advantageously, the control signal is suitable for transmitting control commands for creating the pilot tone signal.

For example, for detection of a rapid movement, (e.g., a heart movement), transmission may be with a high amplitude, for detection of a slow movement, (e.g., a breathing movement), with a low, and for measurements that are movement-sensitive, the pilot tone signal may be switched off.

In one embodiment of the pilot tone signal generator, the control component of the pilot tone signal generator is configured to determine, with the aid of the control signal, generator-specific information for the pilot tone signal generator, in order to specifically control the pilot tone signal generator (in particular as opposed to any other pilot tone signal generators that are arranged on, in and/or around the magnetic resonance tomograph). In particular, the respective pilot tone signal may be impressed on a specific phase and/or amplitude. Advantageously, the pilot tone signals received thereafter may be separated with the aid of these impressed characteristics, for example, by an evaluation unit of the magnetic resonance tomograph.

In one embodiment of the pilot tone signal generator, the pilot tone signal generator includes a transmit antenna, and the pilot tone signal generator is configured to emit a pilot tone signal via the transmit antenna. In particular, the pilot tone signal generator may include a decoupling element for decoupling a transmitter output from signals that the antenna in a magnetic resonance tomograph receives through excitation pulses of the magnetic resonance tomograph. For example, the decoupling element includes a diode or another component with a non-linear characteristic and/or an element with a frequency-dependent characteristic.

In an imaging area of the magnetic resonance tomograph, in which the examination object is located during a magnetic resonance measurement, radio-frequency fields with a power (e.g., in the range of kilowatts) are created to excite the nuclear spins, which may destroy unprotected electronics of the pilot tone signal generator, in particular when the unit is necessarily connected to an antenna that is subjected to the external radio-frequency field. In an advantageous way, the decoupling element makes sure that the output of the pilot tone signal generator is decoupled from the excitation pulses radiated in via the antenna and cannot be destroyed by the pulses.

A magnetic resonance tomograph for examination of an examination object is further proposed. The magnetic resonance tomograph includes an optical transmitter, which is configured to transmit an optical data signal by an optical open-air transmission to at least one pilot tone signal generator. The optical transmitter may be configured to radiate the optical data signal into the patient tunnel and/or to distribute it by scattering on a surface of the patient tunnel.

The optical data signal may be a synchronization signal. The synchronization signal may have a clock signal and/or a control signal.

The magnetic resonance tomograph may include at least one receive coil configured to receive pilot tone signals emitted by the at least one pilot tone signal generator. Advantageously, the at least one receive coil is moreover configured to receive magnetic resonance signals, so that only one receive coil is necessary to receive the pilot tone signals and the magnetic resonance signals.

The magnetic resonance tomograph may include at least one evaluation unit for evaluation of the pilot tone signals received by the receive coil, wherein the evaluation unit is configured, with the aid of the pilot tone signals received by the receive coil, to determine a movement of the examination object. Advantageously, a correction of the movement may be carried out by this, which leads to a better quality of any magnetic resonance images.

The evaluation unit may be configured to separate received pilot tone signals of a plurality of pilot tone signal generators and in particular to assign them entirely or in part to one of a plurality of pilot tone signal generators sending pilot tone signals. Advantageously this enables the various pilot tone signal generators to be controlled individually.

In one embodiment of the magnetic resonance tomograph, the optical transmitter has an amplitude modulator. The amplitude modulator may be configured to carry out a change in light intensity for modulation of the optical signal for the transmission of the optical signal, in particular of the synchronization signal, synchronously. For example, the amplitude modulator may have a sample-and-hold element or flip-flop, which only switches a change of the control signal with one edge of the clock signal to a multiplier of the amplitude modulator. In particular, the amplitude modulator is understood here as an apparatus that is configured, for the optical signal, also to set intermediate stages between the states "off" without light emission and "on" with maximum intensity and thus is differentiated from the switch for digital modulation described below.

Advantageously, a synchronous modulation by the control signal leads to the phase of the modulated synchronization signal, in particular clock signal, not being changed by it and to a PLL on the receive side not being disturbed.

In one embodiment, magnetic resonance tomograph the transmitter is designed, for transmission of the synchronization signal, to switch the optical data signal off and on with a modulation frequency, (e.g., by Amplitude-Shift Keying (ASK) such as On-Off Keying (OOK)), wherein the magnetic resonance tomograph is designed, for transmission of the control signal, to change a frequency of the modulation signal from a first modulation frequency to a second modulation frequency not equal to the first modulation frequency.

Because there is a hard switchover of the intensity of the optical signal in the clock of the modulation frequency, the light sensor delivers a rectangular sensor signal, of which basic frequency corresponds to the first or second modulation frequency. In conjunction with a previously described bandpass filter as part of the signal path for the sensor signal or another filter with frequency-dependent attenuation, advantageously a spectral component (e.g., harmonic, in particular basic frequency) of the rectangular signal is selected for further processing.

The changing of the modulation frequency is as a rule able to be realized significantly more easily and accurately with non-linear light sources, (such as LEDs or semiconductor lasers), than by a direct control of the light intensity. In certain examples, only the modulation frequency with which a switch switches the light intensity on and off is changed.

In one embodiment of the magnetic resonance tomograph, a frequency of the clock signal is an odd-number multiple of the modulation frequency. For example, the clock signal may have a frequency of 12.5 MHz. The modulation frequency may then be switched over between a first modulation frequency and a second modulation frequency, wherein the first modulation frequency in the example relates to 12.5 MHz and the second modulation frequency to a third thereof, e.g., the frequency of the clock signal is equal to the first modulation frequency multiplied by 1 is and equal to the second modulation frequency multiplied by 3. The switchover of the modulation frequency in this case advantageously takes place phase-neutrally, e.g., in the timeframe of the clock frequency or first modulation frequency.

For a modulation of the optical signal by switching on and off, a rectangular signal is generated, which has harmonics at odd-number multiples of the modulation frequency. Thus, if the second modulation frequency is a third of the clock signal frequency, then the third harmonic is at three times the modulation frequency or precisely at the frequency of the clock signal. A bandpass filter in this case enables the spectral component at the clock signal frequency to be selected and all further harmonics to be suppressed or attenuated, e.g., by more than 24 dB, 30 dB, or 36 dB. Thus, both with the first modulation frequency and also with the second modulation frequency, a clock signal of for example 12.5 MHz is provided. Through the phase-neutral switching over between the two modulation frequencies the phase of the transmitted clock signal also remains unchanged in this case, so that downstream PLL circuits may deliver a phase-stable output signal for the pilot tone signal generator. At the same time, however, with a direct-component-free, symmetrical rectangular signal, the amplitude of the third harmonic is only a third as big as the amplitude of the basic wave (first harmonic), whereby an amplitude modulation of the bandpass-filtered receive signal between a third and the full amplitude is produced during the frequency resampling. With this amplitude modulation of the selected spectral components, a control signal may be transmitted, such as for control of the pilot tone signal generation. With a digital code transmitted with this amplitude modulation, different control commands may correspondingly be transmitted, and at the same time a phase-stable clock signal may be provided, wherein the modulation may be provided by a simple switch.

A method for movement correction of a magnetic resonance measurement of an examination object is further proposed. The method includes transmitting a synchronization signal of the magnetic resonance tomograph to at least one pilot tone signal generator, in particular, to a receive unit of the at least one pilot tone signal generator; creating and emitting at least one pilot tone signal with aid of the synchronization signal by the at least one pilot tone signal generator; receiving the pilot tone signal by at least one receive coil of the magnetic resonance tomograph; and carrying out a movement correction with aid of the pilot tone signal.

The advantages of the method for movement correction of a magnetic resonance measurement correspond to the advantages of the pilot tone signal generator and of the magnetic resonance tomograph, which have been set out in detail above. Features, advantages, or alternate forms of embodiment mentioned here may likewise also be transferred to the other claimed subject matter and vice versa.

In other words, the device claims may also be developed with the features that are described or claimed in conjunction with a method. The corresponding functional features of the method in this case are embodied by corresponding physical modules, in particular by hardware modules.

The transmission of the synchronization signal, the creation and emission of the pilot tone signal with the aid of the synchronization signal and the receipt of the pilot tone signal is undertaken during the magnetic resonance measurement. Magnetic resonance signals are thus also acquired as well as the pilot tone signals.

The pilot tone signal generator may be arranged in the immediate vicinity of the heart or the lungs of the examination object. This advantageously enables a higher SNR of the received pilot tone signal to be achieved.

The transmission of the synchronization signal of the magnetic resonance tomograph to the receive unit of a pilot tone signal generator may be undertaken wirelessly, e.g., the synchronization signal is an optical data signal. The synchronization signal may be received with an, in particular first, sensor of the receive unit and output as an output signal.

The creation of the pilot tone signal with the output signal by the pilot tone signal generator may include one or more of the following aspects: (1) filtering of the output signal or of a signal derived therefrom with a filter; (2) stabilization of a clock frequency of an oscillator with the aid of the output signal or with a signal derived therefrom; and/or (3) selection of an odd-numbered harmonic of the output signal or of a signal derived therefrom.

The synchronization signal of the magnetic resonance tomograph may be transmitted to a plurality of pilot tone signal generators. The generator-specific information for the respective pilot tone signal generators may be transmitted by a time-division multiplexing method.

In particular, there is an identification of generator-specific information of the synchronization signal and creation of the respective pilot tone signal as a function of the generator-specific information by the plurality of pilot tone signal generators.

The contributions of the pilot tone signals received by the at least one receive coil of the magnetic resonance tomograph may be separated. Advantageously, this enables the information density of the pilot tone data to be drastically increased, so that an enhanced movement correction is possible.

To carry out the movement correction with the aid of the pilot tone signal, movement-dependent changes of the received pilot tone signal may be recognized by a signal analysis in an evaluation unit of the magnetic resonance tomograph.

BRIEF DESCRIPTION OF THE DRAWINGS

Further advantages, features, and details of the disclosure emerge from the exemplary embodiments described below and also with the aid of the drawings. Parts that correspond to one another are provided with the same reference characters in all figures.

DETAILED DESCRIPTION

Figure 1:
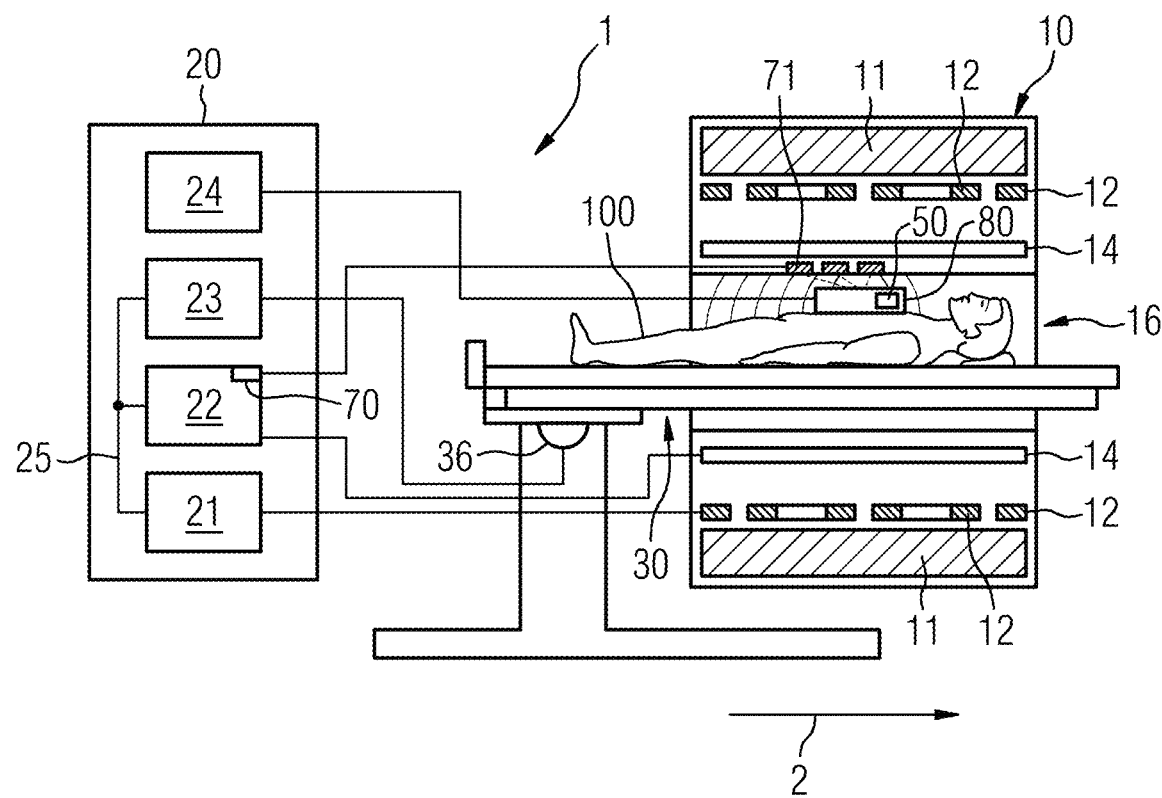
FIG. 1 depicts an example of a magnetic resonance tomograph with a pilot tone signal generator.

FIG. 1 depicts a schematic diagram of a form of embodiment of a magnetic resonance tomograph 1. The magnetic resonance tomograph 1 includes a magnet unit 10, which includes a field magnet 11, which creates a static magnetic field B0 for alignment of nuclear spins of an examination object, here a patient 100, in an imaging area of the magnetic resonance tomograph 1. The imaging area is characterized by a very homogeneous static magnetic field B0, wherein the homogeneity relates in particular to the strength or to the amount of the magnetic field. The imaging area is almost spherical and is arranged in a patient tunnel 16, which extends in a longitudinal direction 2 through the magnet unit 10. A patient table 30 is able to be moved in the patient tunnel 16 by the drive unit 36. The field magnet 11 may include a superconducting magnet, which may provide magnetic fields with a magnetic flux density of up to 3 T, with the latest devices of even more. For lower magnetic field strengths however permanent magnets or electromagnets with normally conducting coils may be used.

The magnet unit 10 furthermore has gradient coils 12 configured, for spatial differentiation of the acquired imaging regions in the examination volume, to superimpose on the magnetic field B0 temporally and spatially variable magnetic fields in three directions. The gradient coils 12 may be coils made of normally conducting wires, which may generate fields orthogonal to one another in the examination volume.

The magnet unit 10 likewise has a body coil 14 configured to radiate a radio-frequency signal supplied via a signal line into the examination volume. It is further conceivable for the body coil 14 to receive magnetic resonance signals emitted by the patient 100 and be able to output them via a signal line; in this case the body coil 14 operates as a receive coil.

A system control unit 20 supplies the magnet unit 10 with the various signals for the gradient coils 12 and the body coil 14 and evaluates the received signals.

The system control unit 20 has a gradient controller 21 configured to supply the gradient coils 12 via supply lines with variable currents that, coordinated with regard to time, provide the desired gradient fields in the examination volume.

The system control unit 20 further has a radio-frequency unit 22 configured to create a radio-frequency pulse with a predetermined time characteristic, amplitude, and spectral power distribution to excite a magnetic resonance of the nuclear spins in the patient 100. In this case, pulse powers in the range of kilowatts may be achieved. The excitation signals may be radiated into the patient 100 via the body coil 14 or also via a local transmit antenna.

A controller 23 communicates via a signal bus 25 with the gradient controller 21 and the radio-frequency unit 22.

Arranged on the patient 100 is a local coil 80 with a pilot tone signal generator 50. The local coil also operates as a receive coil, by accepting and forwarding a magnetic resonance signal from the body of the patient 100. The signal may be forwarded wirelessly, e.g., with a radio link.

Advantageously, the receive coils are broadband enough to not only be able to receive magnetic resonance signals but also pilot tone signals that have a different frequency band from the magnetic resonance signals.

The magnetic resonance signals received by the local coil 80 and pilot tone signals are transmitted to an evaluation unit 24 of the system control unit 20, in which in particular the pilot tone signals are evaluated. If the patient 100 moves during the magnetic resonance measurement, the pilot tone signals are influenced or changed by the movement. From this signal change conclusions may be drawn about the movement of the patient 100. For example, information about the breathing or the heartbeat of the patient may be derived from pilot tone signals. Movement information, which may be employed for movement correction and/or for sequence triggering, may thus be determined with the aid of the evaluation of the pilot tone signals.

The evaluation of the pilot tone signals may be improved if not only the amplitude of the pilot tone signals is evaluated but also its phase angle. The phase angle may in particular be defined relative to a reference clock of the magnetic resonance tomograph 1. The system control unit 20 of the magnetic resonance tomograph 1 has corresponding clock signals available to it internally. For transmission to the pilot tone signal generator 50, the system control unit 20 furthermore has an optical transmitter 70, wherein here a plurality of light emitters 71, which emit the light, is arranged in this case in the patient tunnel 16. The magnetic resonance tomograph may have a plurality of light emitters 71, which are distributed over an inner surface of the patient tunnel 16, or illuminate a light-scattering surface from outside, so that a shading of an optical signal emitted by the light emitters 71 for the pilot tone signal generator 50 is avoided where possible. The light emitters 71 may be LEDs or semiconductor lasers in this case, which are supplied with an electrical signal from the optical transmitter 70 and convert this into the optical signal and emit it into the patient tunnel 16. It is also conceivable for an LED radiator or semiconductor laser to undertake a conversion into light in the optical transmitter 70 and for this to be routed via glass fibers and optional optical splitters to the patient tunnel 16, wherein glass fiber ends are arranged as light emitters 71 in the patient tunnel 16.

Figure 2:
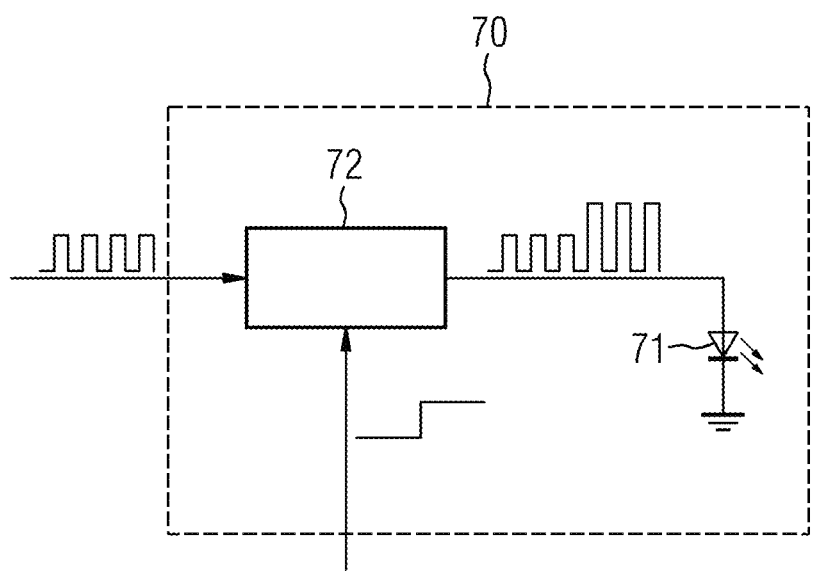
FIG. 2 depicts an optical transmitter of a first embodiment.

Depicted in FIG. 2 is an example of a form of embodiment for an optical transmitter 70 of a magnetic resonance tomograph. The optical transmitter 70 has an amplitude modulator 72. In one case, the amplitude of the signal is modified with the reference clock of the magnetic resonance tomograph 1.

Optionally, a radio-frequency clock signal may be modulated with a low-frequency control signal. For example, the amplitude modulator 72 may have a multiplier, which multiplies the clock signal by a low-frequency control signal. A modulation of the clock signal may be undertaken phase-synchronously, e.g., with the leading and or trailing edge of the clock signal. This may be achieved by the control signal being switched through by a sample-and-hold element to the multiplier, wherein the sample-and-hold element is controlled by the clock signal, e.g., switched through with a low level of the clock signal. An output signal of the amplitude modulator 72 is output directly or via a final stage to one or more LEDs or LED radiators or semiconductor lasers for conversion into an optical signal.

Figure 3:
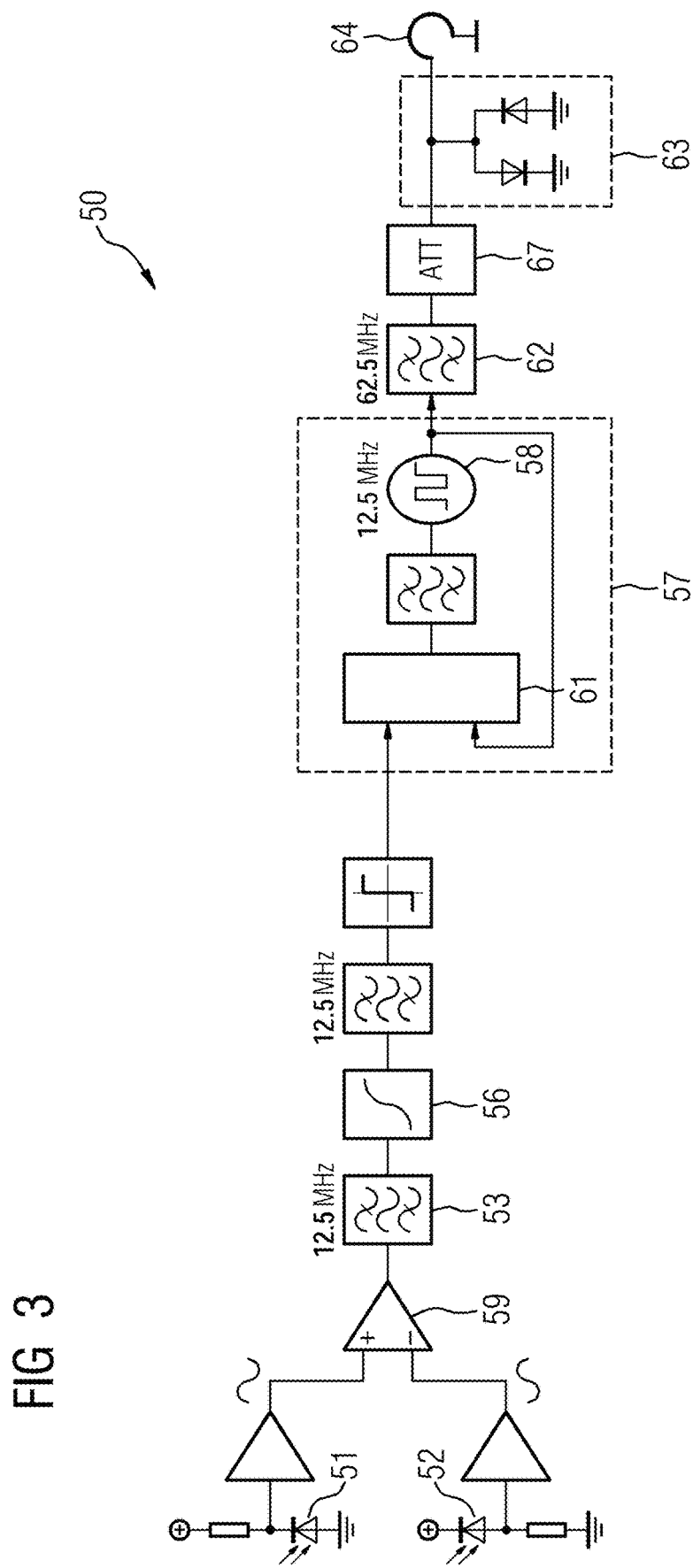
FIG. 3 depicts an example of a pilot tone signal generator that is suitable for processing a clock signal.

Depicted in FIG. 3, in an example of a form of an embodiment, are components of the pilot tone signal generator 50, which are involved in a transmission or recovery of the clock signal and control signal. Other elements of the pilot tone signal generator 50 are not shown for reasons of clarity.

A first optical sensor 51, (e.g., a photodiode with a preamplifier), converts the optical signal into an electrical signal. A filter 53, (e.g., a bandpass filter or lowpass filter), may let through a signal with a frequency of the clock signal and attenuate signals with other frequencies, for example, by more than 24 dB, 30 dB, or 36 dB.

The filtered signal is supplied to further components in order to create a stable master clock for the pilot tone signal generator 50. The filtered signal of the first sensor 51 in this case is first amplified in a limiting amplifier 56 so that the amplitude fluctuations are rectified by the amplitude limiting and only the phase information of the carrier wave remains. In a PLL regulation circuit, the frequency and the phase of an oscillator 58, (e.g., a voltage-controlled quartz oscillator), is stabilized by this. The output signal of the oscillator 58 or of a signal derived therefrom is the master clock for the pilot tone signal generator 50.

A filter 62 selects an odd-number harmonic of an output signal of the Phase-Locked Loop circuit 57. For example, the fifth harmonic of 62.5 MHz of a basic oscillation of 12.5 MHz is selected.

The pilot tone signal generator 50 further includes a transmit antenna 64 for emission of the pilot tone signal. In this example, the transmit antenna 64 with a decoupling element 63 forms a resonant circuit. The decoupling element 63 here includes two antiparallel-switched diodes, which are connected before the transmit antenna 64 to ground. It is thereby provided that a voltage induced by an excitation pulse of the magnetic resonance tomograph 1 into the transmit antenna 64 is limited to below an on-state voltage.

Figure 4:
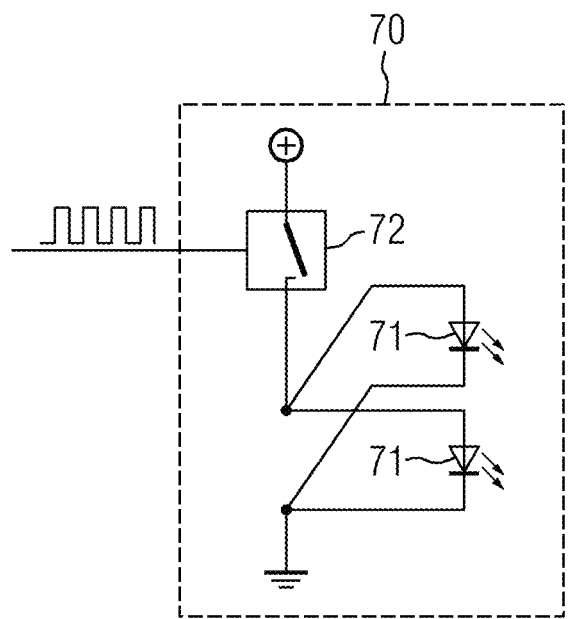
FIG. 4 depicts an optical transmitter of a second embodiment.

Depicted in FIG. 4 is another embodiment for the optical transmitter 70. This form of embodiment is based on the idea that rectangular signals have harmonic components, of which the frequency corresponds to an odd-number frequency of the basic frequency. Shown by way of example here as input signals of the optical transmitter are a rectangular signal with a high frequency, also referred to as the first modulation frequency, (e.g., 12.5 MHz), and a rectangular signal with a lower frequency or second modulation frequency of (12.5/3) MHz. The system control unit 20 provides these signals with high accuracy derived from a stable master clock. Even if the optical transmitter 70 thus emits an optical signal with the second modulation frequency, this then has frequency components with the first modulation frequency of 12.5 MHz.

Clocked by the first modulation signal or the second modulation signal, by an electronic switch, the optical transmitter switches the power supply for the LED or a semiconductor laser as light emitter 71 or light source on and off and in this way creates an optical signal modulated with the rectangular signal. A plurality of LEDs distributed over the patient tunnel 16 may be switched simultaneously in order to avoid a shading of the sensor 51. As an alternative, in an advantageous way, the inner wall of the tunnel may be embodied to scatter light and be illuminated from outside the tunnel. In an advantageous way, a modulation with a rectangular signal is simple to realize with a switch and more efficient than a linear intensity modulation.

Through the switchover between first modulation frequency and second modulation frequency in this case on account of the harmonics, a signal component with the first modulation frequency is also provided here, which is selected by the filter 53 in the pilot tone signal generator. Because the harmonic components have a smaller amplitude than the basic wave, the switchover between the modulation frequencies leads to an amplitude modulation in a spectral range of the first modulation frequency, which for example may be evaluated with the pilot tone signal generator 50 from FIG. 5. If the signals of first modulation frequency and second modulation frequency are in a phase-stable relationship, (e.g., by the edges of the signal with the second modulation frequency being synchronous to edges of the signal with the first modulation frequency), then the clock signal created via a PLL by the frequency sampling is not disturbed. This may be achieved for example by the second modulation frequency being obtained from the first modulation frequency by phase-synchronous frequency division.

Figure 5:
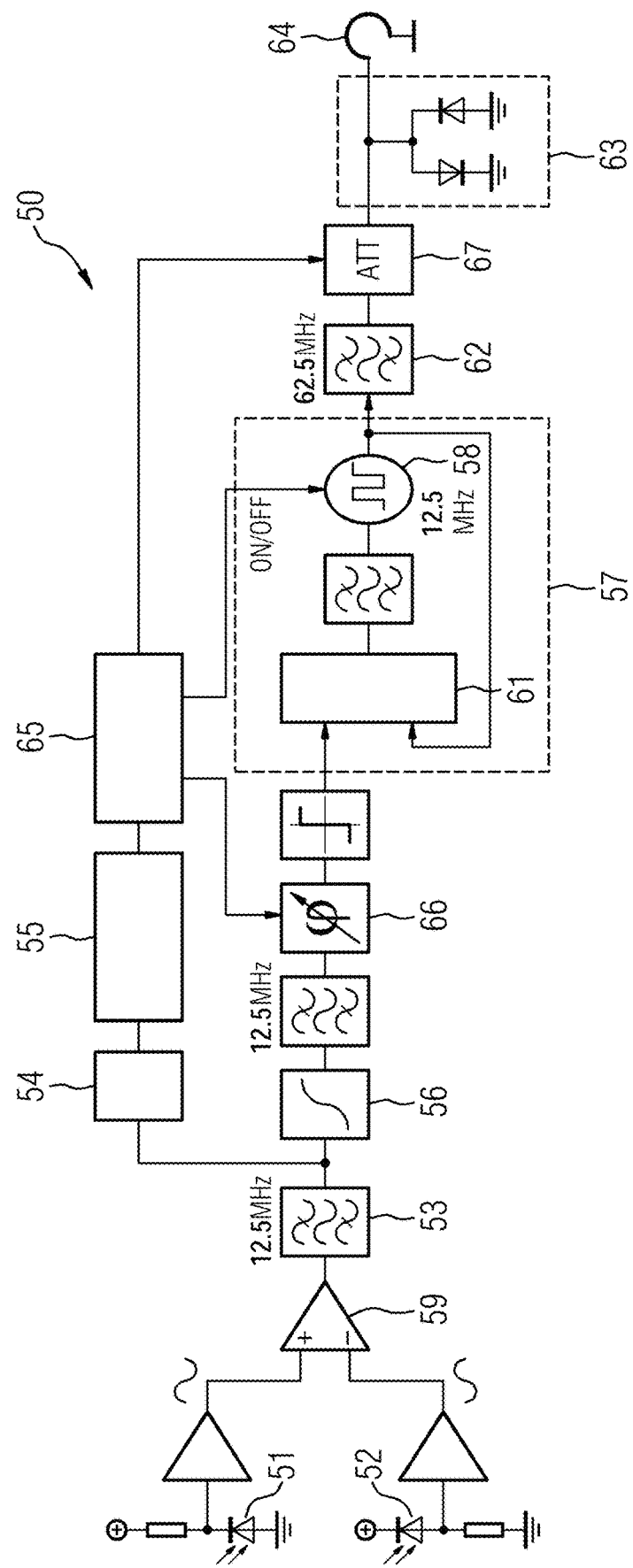
FIG. 5 depicts an example of a pilot tone signal generator that is suitable for processing a clock signal and a control signal.

Depicted in FIG. 5 is a form of embodiment of the pilot tone signal generator expanded when compared to FIG. 3. Here, the filtered signal is supplied in a demodulation branch to an amplitude demodulator 54, in order to retrieve a control signal modulated onto the clock signal. In the simplest case the amplitude demodulator 54 may include a diode as rectifier and a lowpass or buffer capacitor.

The demodulated signal still may have fluctuations, which may be caused by changing shadings on the propagation path in the patient tunnel. These fluctuations may in turn be compensated for with a compensation circuit 55, which is explained for a subsequent figure, FIG. 7.

With a control component 65, with the aid of the control signal of the synchronization signal, a phase control element 66 and/or an amplitude control element 67 may be controlled. Thus, by the control signal, the generation of the pilot tone signal may be controlled. In particular the amplitude may be controlled with the amplitude control element 67 and the phase may be controlled with the phase control element 66. For example, when a rapid movement (e.g., heart movement) is detected, transmission may be with a high pilot tone amplitude, when a slow movement (e.g., breathing movement) is detected with a lower pilot tone amplitude; with magnetic resonance measurements that are not sensitive to movement the pilot tone signal may be switched off.

Optionally, the control component 65 includes an ID decoder, which is embodied to determine generator-specific information, in particular identification information from the control signal for the pilot tone signal generator 50. This is advantageous above all when a plurality of pilot tone signal generators is employed for a magnetic resonance measurement.

With aid of the generator-specific information for the pilot tone signal generator 50, a specific setting of the relative phases and amplitudes may be made possible, in order for example to optimize the "illumination" of the patient 100 with the pilot tone signal. In addition, the amplitudes and phases may be switched on a time scale that is faster than the movement to be detected. Through this time multiplexing method known to the evaluation unit 24, in particular "time/phase multiplexing", it would be possible to separate the amounts of the individual pilot tone signal generators for the overall signal and to markedly increase the information density of the pilot tone data.

Figure 6:
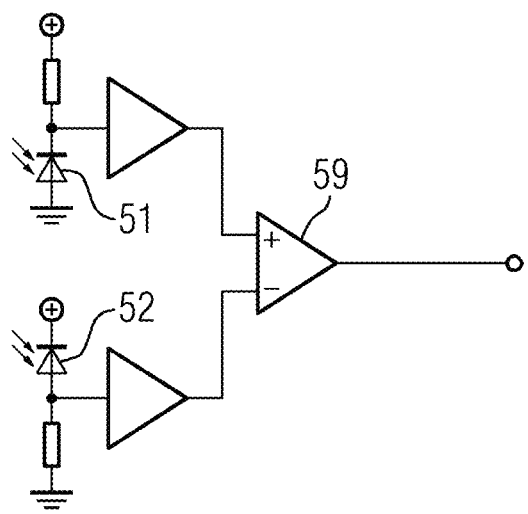
FIG. 6 depicts an example of a receive unit of a pilot tone signal generator.

FIG. 6 depicts a schematic of an advantageous combination of a first sensor 51 and a second sensor 52 for detection of the optical data signal. The combination in particular reduces electromagnetic disturbances to the receipt of the optical data signal, which are caused by the operation of the magnetic resonance tomograph 1.

For this purpose, the first sensor 51 and the second sensor 52 are arranged adjacent to one another, in order to minimize an induction in connecting lines and, where possible, subject both sensors 51, 52 to the same electromagnetic fields. The distance may be less than 2 cm, 1 cm, or 5 mm.

The first sensor 51, here a photodiode in this case, is connected directly in FIG. 6 to the positive supply voltage in the blocking direction, while the connection to the ground potential is made via a resistor.

For the second sensor 52, the roles of resistor and sensor are swapped, the resistor is thus connected directly to the positive supply voltage and the second sensor 52 to the ground potential. The swapping of the arrangement creates a same optical signal in the two sensors 51, 52 an electrical signal with comparable amplitude, but opposing leading signs.

The electrical signal created by the sensors 51, 52 is amplified and supplied to a differential amplifier 59 at the inverting or at the non-inverting input. In an advantageous way, because of the different leading sign, the electrical signals caused by the optical signal to the sensors 51, 52 are added at the output of the differential amplifier 59. Electromagnetic disturbances may induce interference signals with the same leading sign in both branches, so that these cancel each other out in the differential amplifier 59. At the same time, the signal-to-noise ratio of the sum signal is greater by 3 dB than that of the individual signals, because the amounts of noise of the electrical components are uncorrelated and are thus added to each other in power terms, while the correlated receive signals are added to each other in voltage terms.

Figure 7:
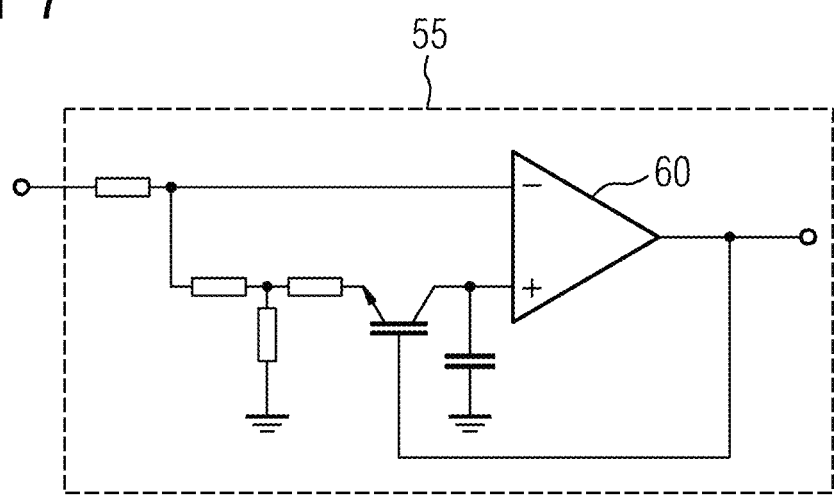
FIG. 7 depicts an example of a compensation circuit of a pilot tone signal generator.

Depicted schematically in FIG. 7 is an embodiment of a compensation circuit 55. The filtered and demodulated sensor signal is supplied to the inverting input of a comparator 60. At the same time, the sensor signal is reduced by a resistive voltage divider, lowpass filtered via an RC element and supplied to the non-inverting input of the comparator 60. The capacitance of the RC element simultaneously serves as a charging capacitance of a track-and-hold element, of which the electrical switch is embodied here as a MOS-FET. The track-and-hold element in this case is activated by the output of the comparator 60, so that the switch of the track-and-hold element is opened when the sensor signal is less than the reference signal. The comparator may be realized, for example, as a differential amplifier with high amplification or as another equivalent circuit.

Figure 8:
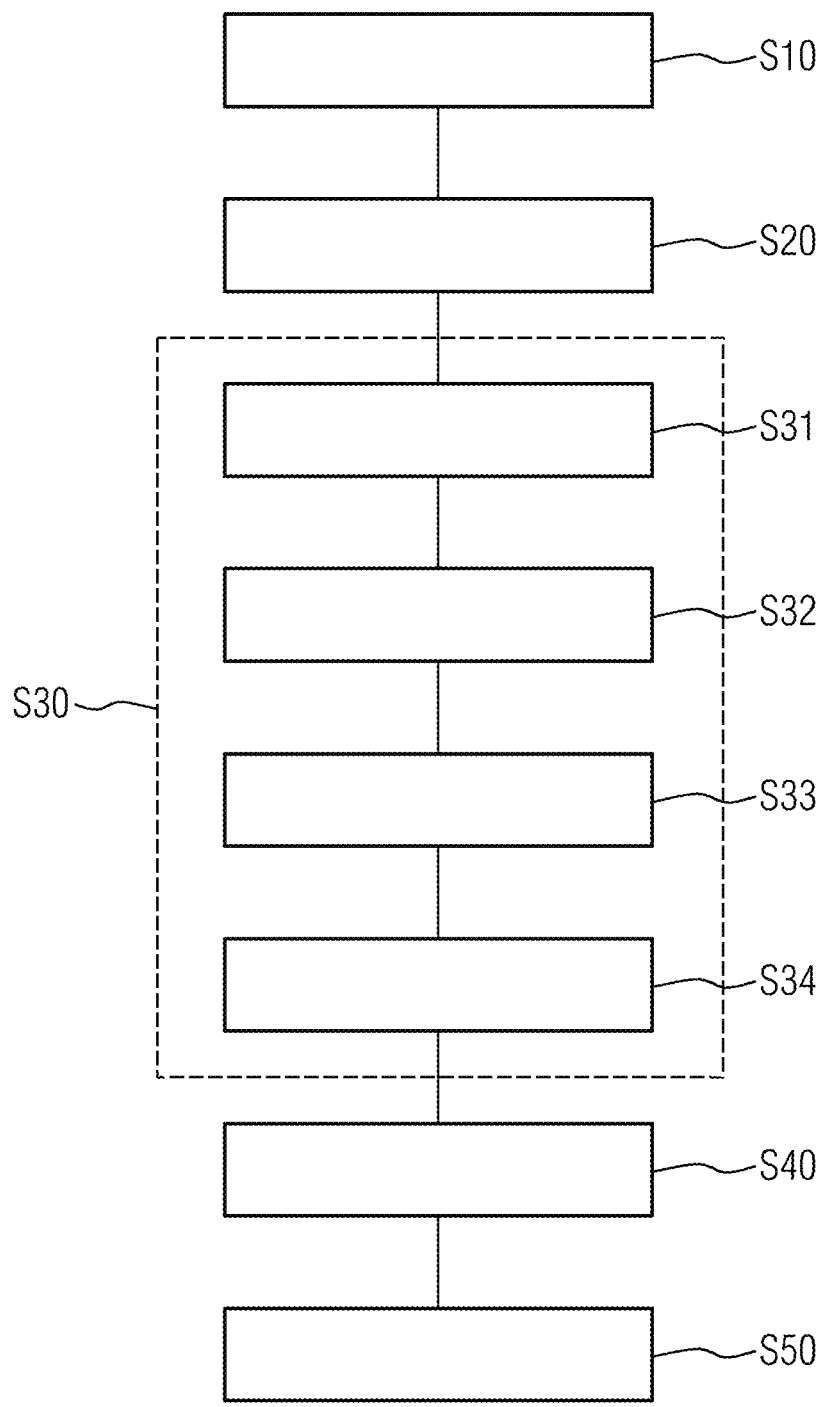
FIG. 8 depicts an example of a method for movement correction of a magnetic resonance measurement with aid of a pilot tone signal generator.

Depicted in FIG. 8 is a method for movement correction of a magnetic resonance measurement of an examination object. In act S10, an examination object (100), (e.g., a patient), is positioned in a magnetic resonance tomograph. In act S20, a synchronization signal of the magnetic resonance tomograph (1) is transmitted to at least one pilot tone signal generator (50), in particular to a receive unit of the at least one pilot tone signal generator.

In act S30, a pilot tone signal is created and emitted with the aid of the synchronization signal by the at least one pilot tone signal generator (50). During creation of the pilot tone signal, in act S31, the output signal and/or a signal derived therefrom is filtered with a filter. In act S32, generator-specific information of the synchronization signal is identified, and a pilot tone signal is created in each case as a function of the generator-specific information by the plurality of pilot tone signal generators. In act S33, a clock frequency of an oscillator is stabilized with the aid of the output signal, or a signal derived therefrom. In act S34, an odd-number harmonic of the output signal or a signal derived therefrom is selected.

It is conceivable for acts S31-S34 to be carried out in a different order, in parallel, and/or repeatedly.

In act S40, the pilot tone signal is received by at least one receive coil of the magnetic resonance tomograph. In act S50, a movement correction and/or a sequence triggering with the aid of the pilot tone signal is carried out.

In conclusion, the methods described in detail above and also the pilot tone signal generators and magnetic resonance tomographs described herein merely involve exemplary embodiments, which may be modified by the person skilled in the art in a wide variety of ways, without departing from the area of the disclosure. Furthermore, the use of the indefinite article "a" or "an" does not exclude the features concerned also being able to be present a plurality of times. Likewise, the terms "unit" and "apparatus" do not exclude the components concerned including a plurality of interoperating sub-components, which may also be spatially distributed.

It is to be understood that the elements and features recited in the appended claims may be combined in different ways to produce new claims that likewise fall within the scope of the present disclosure. Thus, whereas the dependent claims appended below depend on only a single independent or dependent claim, it is to be understood that these dependent claims may, alternatively, be made to depend in the alternative from any preceding or following claim, whether independent or dependent, and that such new combinations are to be understood as forming a part of the present specification.

While the disclosure has been illustrated and described in detail with the help of the embodiments, the disclosure is not limited to the disclosed examples. Other variations may be deduced by those skilled in the art without leaving the scope of protection of the claimed disclosure.

The invention claimed is:

1. A pilot tone signal generator comprising:
a receive unit comprising a first sensor and a second sensor adjacent to the first sensor;
an inverter; and
a summation element,
wherein the first sensor of the receive unit is configured to receive a synchronization signal of a system control unit of a magnetic resonance tomograph,
wherein the synchronization signal comprises a clock signal,
wherein the synchronization signal is an optical data signal,
wherein the first sensor of the receive unit is configured to create a first output signal from the optical data signal,
wherein the second sensor is configured to create a second output signal from the same optical data signal,
wherein the first output signal has an inverse amplitude to the second output signal,
wherein the inverter is configured to invert the first output signal of the first sensor to provide an inverted output signal,
wherein the summation element is configured to add the inverted output signal of the first sensor and the second output signal of the second sensor to provide an electrical sensor signal, and
wherein the pilot tone signal generator is configured to emit a pilot tone signal as a function of the electrical sensor signal.

2. The pilot tone signal generator of claim 1, further comprising:
a Phase-Locked Loop circuit for synchronization of the pilot tone signal,
wherein a signal derived from the electrical sensor signal serves as reference signal for the Phase-Locked Loop circuit.

3. The pilot tone signal generator of claim 2, further comprising:
a filter configured to select a modulation frequency of the electrical sensor signal,
wherein the Phase-Locked Loop circuit is configured to stabilize an oscillator as a function of the modulation frequency.

4. The pilot tone signal generator of claim 3, wherein the Phase-Locked Loop circuit is further configured to stabilize the oscillator as a function of a modulation phase.

5. The pilot tone signal generator of claim 3, wherein the filter is further configured to select an odd-number harmonic of an output signal of the Phase-Locked Loop circuit.

6. The pilot tone signal generator of claim 2, further comprising:
a filter configured to select an odd-number harmonic of an output signal of the Phase-Locked Loop circuit.

7. The pilot tone signal generator of claim 1, further comprising:
an amplitude demodulator having a compensation circuit,
wherein the amplitude demodulator is configured to compensate for a low-frequency signal component of the electrical sensor signal compared to a modulation frequency of the electrical sensor signal.

8. The pilot tone signal generator of claim 1, further comprising:
a control component,
wherein the synchronization signal comprises a control signal,
wherein the control component is configured to control, with aid of the control signal, an amplitude, and/or phase of the pilot tone signal.

9. The pilot tone signal generator of claim 8, wherein the control component of the pilot tone signal generator is configured to determine, with the aid of the control signal, generator-specific information for the pilot tone signal generator in order to specifically control the pilot tone signal generator.

10. The pilot tone signal generator of claim 1, wherein the first sensor and the second sensor are positioned less than 2 cm from each other.

11. A magnetic resonance tomograph system comprising:
a pilot tone signal generator; and
an optical transmitter configured to transmit an optical data signal by an optical open-air transmission to the pilot tone signal generator,
wherein the pilot tone signal generator comprises:
a receive unit comprising a first sensor and a second sensor adjacent to the first sensor;
an inverter; and
a summation element, wherein the first sensor of the receive unit is configured to receive a synchronization signal of a system control unit of a magnetic resonance tomograph, wherein the synchronization signal comprises a clock signal, wherein the synchronization signal is the optical data signal, wherein the first sensor of the receive unit is configured to create a first output signal from the optical data signal, wherein the second sensor is configured to create a second output signal from the same optical data signal, wherein the first output signal has an inverse amplitude to the second output signal, wherein the inverter is configured to invert the first output signal of the first sensor to provide an inverted output signal, wherein the summation element is configured to add the inverted output signal of the first sensor and the second output signal of the second sensor to provide an electrical sensor signal, and wherein the pilot tone signal generator is configured to emit a pilot tone signal as a function of the electrical sensor signal.

12. The magnetic resonance tomograph system of claim 11, further comprising:
at least one receive coil configured to receive pilot tone signals emitted by the pilot tone signal generator.

13. The magnetic resonance tomograph system of claim 11, further comprising:
an evaluation unit configured to separate received pilot tone signals of a plurality of pilot tone signal generators.

14. The magnetic resonance tomograph system of claim 11, wherein the optical transmitter is configured to radiate the optical data signal into a patient tunnel and/or to distribute the optical data signal by scattering on a surface of the patient tunnel.

15. A method for movement correction of a magnetic resonance measurement, the method comprising:

transmitting a synchronization signal of a magnetic resonance tomograph to a receive unit of a pilot tone signal generator;

receiving, by a first sensor of the receive unit of the pilot tone signal generator, the synchronization signal, wherein the synchronization signal comprises a clock signal, and wherein the synchronization signal is an optical data signal;

creating, by the first sensor of the receive unit, a first output signal from the optical data signal;

creating, by a second sensor of the receive unit a second output signal from the same optical data signal, wherein the second sensor is positioned adjacent to the first sensor, and wherein the first output signal has an inverse amplitude to the second output signal;

inverting, by an inverter of the pilot tone signal generator, the first output signal of the first sensor to provide an inverted output signal;

adding, by a summation element of the pilot tone signal generator, the inverted output signal of the first sensor and the second output signal of the second sensor to provide an electrical sensor signal;

emitting, by the pilot tone signal generator, a pilot tone signal as a function of the electrical sensor signal;

receiving the pilot tone signal by at least one receive coil of the magnetic resonance tomograph; and carrying out a movement correction and/or a sequence triggering with aid of the pilot tone signal.

* * * * *